United States Patent [19]
Baeck et al.

[11] Patent Number: 5,922,082
[45] Date of Patent: Jul. 13, 1999

[54] DETERGENT COMPOSITION CONTAINING WOOL COMPATIBLE HIGH ALKALINE PROTEASES

[75] Inventors: Andre Cesar Baeck, Bonheiden; Ann Katrien Marie Agnes Verschuere, Beernem; Alfred Busch, Londerzeel, all of Belgium

[73] Assignee: Procter & Gamble Company, Cincinnati, Ohio

[21] Appl. No.: 08/750,406

[22] PCT Filed: May 23, 1995

[86] PCT No.: PCT/US95/06481

§ 371 Date: Dec. 6, 1996

§ 102(e) Date: Dec. 6, 1996

[87] PCT Pub. No.: WO95/34627

PCT Pub. Date: Dec. 21, 1995

[30] Foreign Application Priority Data

Jun. 16, 1994 [EP] European Pat. Off. .............. 94870096

[51] Int. Cl.⁶ .............................. C11D 3/386; C11D 3/37; C11D 1/83; D06B 1/00
[52] U.S. Cl. .............................. 8/137; 510/292; 510/300; 510/320; 510/350; 510/360; 510/392; 510/466; 510/474; 510/475; 510/499; 510/530
[58] Field of Search .................................... 510/292, 300, 510/320, 360, 392, 475, 499, 466, 474, 350, 530; 8/137

[56] References Cited

U.S. PATENT DOCUMENTS

| | | | |
|---|---|---|---|
| H1513 | 1/1996 | Murch et al. | 252/546 |
| H1514 | 1/1996 | Willmon et al. | 252/547 |
| H1635 | 3/1997 | Vander Meer | 510/220 |
| 5,047,165 | 9/1991 | Lysy et al. | 252/121 |
| 5,204,015 | 4/1993 | Caldwell et al. | 252/174.12 |
| 5,259,994 | 11/1993 | Welch et al. | 252/542 |
| 5,500,153 | 3/1996 | Figueroa et al. | 252/548 |
| 5,560,748 | 10/1996 | Surutzidis et al. | 8/111 |
| 5,565,145 | 10/1996 | Watson et al. | 510/350 |
| 5,677,272 | 10/1997 | Ghosh et al. | 510/306 |
| 5,679,630 | 10/1997 | Baeck et al. | 510/305 |
| 5,707,950 | 1/1998 | Kusturi et al. | 510/320 |

FOREIGN PATENT DOCUMENTS

| | | |
|---|---|---|
| 0581751 | 2/1994 | European Pat. Off. . |
| 0582478 | 2/1994 | European Pat. Off. . |
| 3582478 | 2/1994 | European Pat. Off. . |
| 0628624 | 12/1994 | European Pat. Off. . |

*Primary Examiner*—Kery Fries
*Attorney, Agent, or Firm*—C. Brant Cook; Kim W. Zerby; Jacobus C. Rasser

[57] ABSTRACT

The invention relates to a detergent composition having a wool compatible high alkaline protease with at least one mutation in each of the regions 96–110 and 123–135 according to the BPN'-numbering. The detergent composition is preferably substantially free of bleach and does contain so-called dye transfer inhibition technology.

17 Claims, No Drawings

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 275 amino acids
      (B) TYPE: amino acid
      (D) TOPOLOGY: linear (ii) MOLECULE TYPE: protein (ix) FEATURE:
      (D) OTHER INFORMATION: Xaa = deletion or absent amino acid (xi) SEQUENCE DESCRIPTION: SEQ ID NO:1:

```
Ala Gln Ser Val Pro Trp Gly Ile Ser Arg Val Gln
 1               5                  10
Ala Pro Ala Ala His Asn Arg Gly Leu Thr Gly Ser
            15                  20
Gly Val Lys Val Ala Val Leu Asp Thr Gly Ile Xaa
25                  30                  35
Ser Thr His Pro Asp Leu Asn Ile Arg Gly Gly Ala
            40                  45
Ser Phe Val Pro Gly Glu Xaa Pro Ser Thr Gln Asp
    50                  55                  60
Gly Asn Gly His Gly Thr His Val Ala Gly Thr Ile
            65                  70
Ala Ala Leu Asn Asn Ser Ile Gly Val Leu Gly Val
            75                  80
Ala Pro Ser Ala Glu Leu Tyr Ala Val Lys Val Leu
85                  90                  95
Gly Ala Ser Gly Ser Gly Ser Val Ser Ser Ile Ala
            100                 105
Gln Gly Leu Glu Trp Ala Gly Asn Asn Gly Met His
            110                 115                 120
Val Ala Asn Leu Ser Leu Gly Ser Pro Ser Pro Ser
                125                 130
Ala Thr Leu Glu Gln Ala Val Asn Ser Ala Thr Ser
            135                 140
Arg Gly Val Leu Val Ala Ala Ser Gly Asn Ser
145                 150                 155
Gly Ala Gly Ser Xaa Xaa Xaa Xaa Ile Ser Tyr Pro
            160                 165
Ala Arg Tyr Ala Asn Ala Met Ala Val Gly Ala Thr
    170                 175                 180
Asp Gln Asn Asn Asn Arg Ala Ser Phe Ser Gln Tyr
                185                 190
Gly Ala Gly Leu Asp Ile Val Ala Pro Gly Val Asn
            195                 200
Val Gln Ser Thr Tyr Pro Gly Ser Thr Tyr Ala Ser
205                 210                 215
Leu Asn Gly Thr Ser Met Ala Thr Pro His Val Ala
            220                 225
```

```
Gly Ala Ala Ala Leu Val Lys Gln Lys Asn Pro Ser
    230             235             240

Trp Ser Asn Val Gln Ile Arg Asn His Leu Lys Asn
            245             250

Thr Ala Thr Ser Leu Gly Ser Thr Asn Leu Tyr Gly
        255             260

Ser Gly Leu Val Asn Ala Glu Ala Ala Thr Arg
265             270             275
```

DETERGENT COMPOSITION CONTAINING WOOL COMPATIBLE HIGH ALKALINE PROTEASES

FIELD OF THE INVENTION

The present invention relates to substantially bleach free detergent compositions comprising variants of the high alkaline protease having high homology with the amino acid sequence of Bacillus lentus protease. Said variants having at least one mutation in each of the regions 96–110 and 123–135 (BPN'-numbering), i.e. at least one mutation in both sites of the so-called "S1–S4 substrate binding pockets" (Int. symposium on subtilisin enzymes, Hamburg, Germany Sep. 24–25, 1992; R. J. Siezen).

More in particular, the present invention relates to detergent compositions comprising said mutated protease and in addition a polymeric dye transfer inhibiting agent to be used for treatment of fabrics, more specifically washing of colored fabrics and demonstrating high care on wool and/or silk fabrics.

BACKGROUND OF THE INVENTION

Enzymes make up a very important class of naturally occuring proteins. Each class of enzyme catalyzes a different kind of chemical reaction. One class of enzymes, known as proteases, are known for their ability to hydrolyze (break down a compound into two or more smaller compounds with the uptake of the H and OH parts of a water molecule on either side of the chemical bond cleaved) other proteins. This ability to hydrolyze proteins has been taken advantage of by incorporating naturally occurring and protein engineered proteases as an additive to laundry detergent preparations. Many stains and soils on clothes are proteinaceous and water-insoluble. Wide-specificity proteases can substantially improve removal of such stains by hydrolyzing the water-insoluble proteins into smaller water-soluble fragments.

Unfortunately, the efficacy level of these proteins in their natural environment, frequently does not translate when applied into the relatively unnatural wash environment. Specifically, protease characteristics such as thermal stability, pH stability, oxidative stability and substrate specificity are not necessarily optimized for utilization outside the natural environment of the enzyme. Moreover cleaning/stain removal performance and fabric care, more specifically wool/silk compatibility are not necessarily optimized.

Considering a specific type of protease (e.g. subtilisins of *B. amyloliquefaciens, B. lentus, B. licheniformis* etc.), the amino acid sequence of the protease enzyme determines the characteristics of the protease. Changing the amino acid sequence of the protease may alter the properties of the enzyme to varying degrees, or may even inactivate the enzyme, depending upon the location, nature and/or magnitude of the change in the amino acid sequence. Several approaches have been taken to alter the amino acid sequence of proteases in an attempt to improve their properties, with the goal of increasing the efficacy of the protease for cleaning uses such as in the wash environment. These approaches include altering the amino acid sequence to enhance thermal stability, proteolytic activity, oxidation stability, etc. under quite diverse conditions.

Despite the variety of approaches described in the art, there is a continuing need for new effective variants of proteases useful for cleaning a variety of fabrics without damaging the textile properties. It is therefore an object of the present invention to provide detergent compositions substantially free of bleach containing high alkaline protease enzymes combining excellent cleaning/stain removal performance to good wool and/or silk compatibility.

DETAILED DESCRIPTION OF THE INVENTION

High alkaline proteases suitable for detergent compositions have high homology (at least 70%) with the amino acid sequence shown in FIG. 1. This sequence is identical to Bacillus lentus subtilisin (BPN' numbering). Some commercially available high alkaline proteases such as Savinase, Durazym, Maxacal, Maxapem, Opticlean etc. have either the same amino acid sequence or hardly differ from it (up to 2 amino acids). However, when used in substantially bleach free detergent compositions they all Lack the necessary wool/silk compatibility in that they show high damage on such fabrics.

It has now surprisingly been found that specific variants of such high alkaline proteases having the amino acid sequence according to FIG. 1 (BPN' numbering) with at least one mutation in each of the regions 96–110 and 123–135 demonstrate a good wool fabric compatibility and maintain an excellent washing performance.

Accordingly, the present invention provides detergent compositions substantially free of bleach comprising a high alkaline protease with the amino acid sequence according to FIG. 1 (BPN' numbering) having at least one mutation in each of the regions 96–110 and 123–135. The proteases are obtainable by methods known and described in the literature, e.g. by cultivation of a protease producing strain (for instance *Bacillus lentus*) in a suitable nutrient medium, containing carbon and nitrogen sources and inorganic salts, followed by the recovery of the enzyme desired, or may e.g. be produced by employing recombinant DNA technology.

A preferred protease according to the invention to be used in the substantially bleach free detergent composition and showing an excellent compatibility for wool and/or silk fabrics is the protease with a mutation at position V104, preferably from Valine into Isoleucine (V104I) or into tyrosine (V104Y) and a mutation at position N123, preferably from Asparagine into Serine (N123S).

In addition, mutations in and/or outside the regions mentioned, e.g. at positions 27, 76, 99, 101, 103, 222, 274 and mixtures thereof 27, 76, 99, 101, 103 and/or 222 result in improved stability and/or activity of the proteases according to the invention without hampering the fabric compatibility. Non-limiting examples of mutations are K27R, N76D, S99D, S101R, S103A, M222S, M222A, M222C and T274A.

In addition the detergent compositons having above protease contain a polymeric dye transfer inhibiting agent selected from polyamine N-oxide polymers, copolymers of N-vinylpyrrolidone and N-vinylimidazole, polyvinylpyrrolidones, polyvinyloxazolidones, polyvinylimidazoles or mixtures thereof.

The density of the compositions herein ranges from 550 to 950 g/liter, preferably 600 to 900 g/liter of composition measured at 20° C.

The "compact" form of the compositions herein is best reflected, in terms of composition, by the amount of inorganic filler salt; inorganic filler salts are conventional ingredients of detergent compositions in powder form; in conventional detergent compositions, the filler salts are present in substantial amounts, typically 17–35% by weight of the total composition.

In the compact compositions, the filler salt is present in amounts not exceeding 15% of the total composition, preferably not exceeding 10%, most preferably not exceeding 5% by weight of the composition.

Inorganic filler salts, such as meant in the present compositions are selected from the alkali and alkaline-earth-metal salts of sulphates and chlorides.

A preferred filler salt is sodium sulphate.

Protease

Suitable high alkaline proteases are variants of proteases known in the literature as *B. lentus* subtilisin, subtilisin 309, *B. alkalophilus* subtilisin, PB 92 subtilisin or have an amino acid sequence with at least 70% homology. Other suitable proteases are variants of proteases which show a positive immunological cross-reaction with the antibody of the proteases as described hereinabove.

The proteases according to the present invention are present in an amount from 0.001% to 2%, preferably from 0.001% to 1%, more preferably from 0.002% to 0.5% of active enzyme by weight of the detergent composition.

In the context of this invention a subtilisin is defined as a serine protease produced by gram-positive bacteria or fungi. According to another definition, a subtilisin is a serine protease, wherein the relative order of the amino acid residues in the catalytic triad is Asp-His-Ser (positions 32, 64 and 221, BPN' numbering).

Amino Acids

As abbreviations for amino acids the following symbols are used:

A=Ala=Alanine
C=Cys=Cysteine
D=Asp=Aspartic acid
E=Glu=Glutamic acid
F=Phe=Phenylalanine
G=Gly=Glycine
H=His=Histidine
I=Ile=Isoleucine
K=Lys=Lysine
L=Leu=Leucine
M=Met=Methionine
N=Asn=Asparagine
P=Pro=Proline
Q=Gln=Glutamine
R=Arg=Arginine
S=Ser=Serine
T=Thr=Threonine
V=Val=Valine
W=Trp=Tryptophan
Y=Tyr=Tyrosine
B=Asx=Asp (D) or Asn (N)
Z=Glx=Glu(E) or Gln(Q)
X=an arbitrary amino acid
Xaa=deletion or absent amino acid Protease Variants By a protease variant or mutated protease is meant a protease obtainable by alteration of a DNA nucleotide sequence of the parent gene or its derivatives. The protease variant or mutated protease may be expressed and produced when the DNA nucleotide sequence encoding the protease is inserted into a suitable vector in a suitable host organism. The host organism is not necessarily identical to the organism from which the parent gene originated.

Amino Acid Numbering

In the context of this invention a specific numbering of amino acid residue positions in subtilisins is employed. By alignment of the amino acid sequences of various subtilisins along with subtilisin BPN', it is possible to allot a number to the amino acid residue position in any subtilisin to the number of the analogous amino acid position in subtilisin BPN' ("BPN' numbering", vide e.g. International Patent Publication Nos. WO 89/06279 and WO 91/00345).

In describing the various protease variants produced or contemplated according to the invention, the following nomenclatures were adapted for ease of reference:

[Original amino acid; Position; Substituted amino acid].

For example, the substitution of valine with isoleucine in position 104 is designated as V104I.

All positions mentioned in this context refer to the BPN' numbers described above.

Proteolytic Activity

In the context of this invention proteolytic activity is expressed in Kilo NOVO Protease Units (KNPU). The activity is determined relatively to an enzyme standard (SAVINASE™) and the determination is based on the digestion of a dimethyl casein (DMC) solution by the proteolytic enzyme at standard conditions, i.e. 50° C., pH 8.3,9 min. reaction time, 3 min. measuring time.

POLYMERIC DYE TRANSFER INHIBITING AGENTS

The detergent compositions according to the present invention also comprise from 0.001% to 10%, preferably from 0.01% to 2%, more preferably from 0.05% to 1% by weight of polymeric dye transfer inhibiting agents. Said polymeric dye transfer inhibiting agents are normally incorporated into detergent compositions in order to inhibit the transfer of dyes from colored fabrics onto fabrics washed therewith. These polymers have the ability to complex or adsorb the fugitive dyes washed out of dyed fabrics before the dyes have the opportunity to become attached to other articles in the wash. Especially suitable polymeric dye transfer inhibiting agents are polyamine N-oxide polymers, copolymers of N-vinylpyrrolidone and N-vinylimidazole, polyvinylpyrrolidone polymers, polyvinyloxazolidones and polyvinylimidazoles or mixtures thereof.

a) Polyamine N-oxide polymers

The polyamine N-oxide polymers suitable for use contain units having the following structure formula:

(I)

wherein

P is a polymerisable unit, whereto the R-N-O group can be attached to or wherein the R-N-O group forms part of the polymerisable unit or a combination of both.

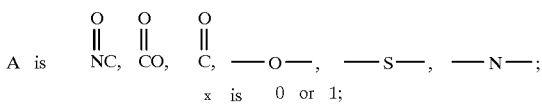

R are aliphatic, ethoxylated aliphatics, aromatic, heterocyclic or alicyclic groups or any combination thereof whereto the nitrogen of the N-O group can be attached or wherein the nitrogen of the N-O group is part of these groups.

The N-O group can be represented by the following general structures:

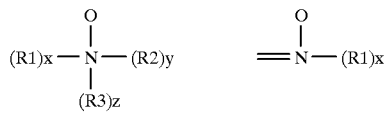

wherein
R1, R2, and R3 are aliphatic groups, aromatic, heterocyclic or alicyclic groups or combinations thereof, x or/and y or/and z is 0 or 1 and wherein the nitrogen of the N-O group can be attached or wherein the nitrogen of the N-O group forms part of these groups.

The N-O group can be part of the polymerisable unit (P) or can be attached to the polymeric backbone or a combination of both.

Suitable polyamine N-oxides wherein the N-O group forms part of the polymerisable unit comprise polyamine N-oxides wherein R is selected from aliphatic, aromatic, alicyclic or heterocyclic groups.

One class of said polyamine N-oxides comprises the group of polyamine N-oxides wherein the nitrogen of the N-O group forms part of the R-group. Preferred polyamine N-oxides are those wherein R is a heterocyclic group such as pyrridine, pyrrole, imidazole, pyrrolidine, piperidine, quinoline, acridine and derivatives thereof.

Another class of said polyamine N-oxides comprises the group of polyamine N-oxides wherein the nitrogen of the N-O group is attached to the R-group.

Other suitable polyamine N-oxides are the polyamine oxides whereto the N-O group is attached to the polymerisable unit. Preferred class of these polyamine N-oxides are the polyamine N-oxides having the general formula (I) wherein R is an aromatic, heterocyclic or alicyclic groups wherein the nitrogen of the N-0 functional group is part of said R group.

Examples of these classes are polyamine oxides wherein R is a heterocyclic compound such as pyrridine, pyrrole, imidazole and derivatives thereof.

Another preferred class of polyamine N-oxides are the polyamine oxides having the general formula (I) wherein R are aromatic, heterocyclic or alicyclic groups wherein the nitrogen of the N-0 functional group is attached to said R groups.

Examples of these classes are polyamine oxides wherein R groups can be aromatic such as phenyl.

Any polymer backbone can be used as long as the amine oxide polymer formed is water-soluble and has dye transfer inhibiting properties. Examples of suitable polymeric backbones are polyvinyls, polyalkylenes, polyesters, polyethers, polyamide, polyimides, polyacrylates and mixtures thereof.

The amine N-oxide polymers of the present invention typically have a ratio of amine to the amine N-oxide of 10:1 to 1:1000000. However the amount of amine oxide groups present in the polyamine oxide polymer can be varied by appropriate copolymerization or by appropriate degree of N-oxidation. Preferably, the ratio of amine to amine N-oxide is from 2:3 to 1:1000000. More preferably from 1:4 to 1:1000000, most preferably from 1:7 to 1:1000000. The polymers of the present invention actually encompass random or block copolymers where one monomer type is an amine N-oxide and the other monomer type is either an amine N-oxide or not. The amine oxide unit of the polyamine N-oxides has a PKa<10, preferably PKa<7, more preferred PKa<6.

The polyamine oxides can be obtained in almost any degree of polymerisation. The degree of polymerisation is not critical provided the material has the desired water-solubility and dye-suspending power.

Typically, the average molecular weight is within the range of 500 to 1000,000; preferably from 1,000 to 50,000, more preferably from 2,000 to 30,000, most preferably from 3,000 to 20,000.

b) Copolymers of N-vinylpyrrolidone and N-vinylimidazole

The N-vinylimidazole N-vinylpyrrolidone polymers used in the present invention have an average molecular weight range from 5,000–1,000,000, preferably from 20,000–200, 000.

Highly preferred polymers for use in detergent compositions according to the present invention comprise a polymer selected from N-vinylimidazole N-vinylpyrrolidone copolymers wherein said polymer has an average molecular weight range from 5,000 to 50,000 more preferably from 8,000 to 30,000, most preferably from 10,000 to 20,000.

The average molecular weight range was determined by light scattering as described in Barth H. G. and Mays J. W. Chemical Analysis Vol 113, "Modern Methods of Polymer Characterization".

Highly preferred N-vinylimidazole N-vinylpyrrolidone copolymers have an average molecular weight range from 5,000 to 50,000; more preferably from 8,000 to 30,000; most preferably from 10,000 to 20,000.

The N-vinylimidazole N-vinylpyrrolidone copolymers characterized by having said average molecular weight range provide excellent dye transfer inhibiting properties while not adversely affecting the cleaning performance of detergent compositions formulated therewith.

The N-vinylimidazole N-vinylpyrrolidone copolymer of the present invention has a molar ratio of N-vinylimidazole to N-vinylpyrrolidone from 1 to 0.2, more preferably from 0.8 to 0.3, most preferably from 0.6 to 0.4.

c) Polyvinylpyrrolidone

The detergent compositions of the present invention may also utilize polyvinylpyrrolidone ("PVP") having an average molecular weight of from about 2,500 to about 400,000, preferably from about 5,000 to about 200,000, more preferably from about 5,000 to about 50,000, and most preferably from about 5,000 to about 15,000. Suitable polyvinylpyrrolidones are commercially vailable from ISP Corporation, New York, N.Y. and Montreal, Canada under the product names PVP K-15 (viscosity molecular weight of 10,000), PVP K-30 (average molecular weight of 40,000), PVP K-60 (average molecular weight of 160,000), and PVP K-90 (average molecular weight of 360,000). PVP K-15 is also available from ISP Corporation. Other suitable polyvinylpyrrolidones which are commercially available from BASF Cooperation include Sokalan HP 165 and Sokalan HP 12. Polyvinylpyrrolidones known to persons skilled in the detergent field; see for example EP-A-262,897 and EP-A-256,696.

d) Polyvinyloxazolidone

The detergent compositions of the present invention may also utilize polyvinyloxazolidone as a polymeric dye transfer inhibiting agent. Said polyvinyloxazolidones have an average molecular weight of from about 2,500 to about 400,000, preferably from about 5,000 to about 200,000, more preferably from about 5,000 to about 50,000, and most preferably from about 5,000 to about 15,000.

e) Polyvinylimidazole

The detergent compositions of the present invention may also utilize polyvinylimidazole as polymeric dye transfer inhibiting agent. Said polyvinylimidazoles have an average about 2,500 to about 400,000, preferably from about 5,000 to about 200,000, more preferably from about 5,000 to about 50,000, and most preferably from about 5,000 to about 15,000.

SURFACTANT SYSTEM

The detergent compositions according to the present invention comprise a surfactant system which is substantially free of bleach and wherein the surfactant can be selected from nonionic and/or anionic and/or cationic and/or ampholytic and/or zwitterionic and/or semi-polar surfactants.

Preferred non-alkylbenzene sulfonate surfactant systems to be used according to the present invention comprise as a surfactant one or more of the nonionic and/or anionic surfactants described herein. These surfactants have found to be very useful in combination with the polymeric dye transfer inhibiting agents/proteases combination of the the present invention.

Polyethylene, polypropylene, and polybutylene oxide condensates of alkyl phenols are suitable for use as the nonionic surfactant of the surfactant systems of the present invention, with the polyethylene oxide condensates being preferred. These compounds include the condensation products of alkyl phenols having an alkyl group containing from about 6 to about 14 carbon atoms, preferably from about 8 to about 14 carbon atoms, in either a straight-chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available nonionic surfactants of this type include Igepal™ CO-630, marketed by the GAF Corporation; and Triton™ X-45, X-114, X-100 and X-102, all marketed by the Rohm & Haas Company. These surfactants are commonly referred to as alkylphenol alkoxylates (e.g., alkyl phenol ethoxylates).

The condensation products of primary and secondary aliphatic alcohols with from about 1 to about 25 moles of ethylene oxide are suitable for use as the nonionic surfactant of the nonionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. Examples of commercially available nonionic surfactants of this type include Tergitol™ 15-S-9 (the condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-6.5 (the condensation product of $C_{12}$–$C_{13}$ linear alcohol with 6.5 moles of ethylene oxide), Neodol™ 45-7 (the condensation product of $C_{14}$–$C_{15}$ linear alcohol with 7 moles of ethylene oxide), Neodol™ 45-4 (the condensation product of $C_{14}$–$C_{15}$ linear alcohol with 4 moles of ethylene oxide) marketed by Shell Chemical Company, and Kyro™ EOB (the condensation product of $C_{13}$–$C_{15}$ alcohol with 9 moles ethylene oxide), marketed by The Procter & Gamble Company.

Also useful as the nonionic surfactant of the surfactant systems of the present invention are the alkylpolysaccharides disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6- positions on the preceding saccharide units.

The preferred alkylpolyglycosides have the formula

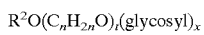

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominately the 2-position.

Other suitable nonionic surfactants are the condensation products of ethylene oxide with a hydrophobic base formed by the condensation of propylene oxide with propylene glycol are also suitable for use as the additional nonionic surfactant of the nonionic surfactant systems of the present invention. The hydrophobic portion of these compounds will preferably have a molecular weight of from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially-available Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic™ compounds, marketed by BASF.

Preferred for use as the nonionic surfactant of the surfactant systems of the present invention are polyethylene oxide condensates of alkyl phenols, condensation products of primary and secondary aliphatic alcohols with from about 1 to about 25 moles of ethylene oxide, alkylpolysaccharides, and mixtures thereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Highly preferred nonionic surfactants are polyhydroxy fatty acid amide surfactants of the formula.

wherein $R^1$ is H, or $R^1$ is $C_{1-4}$ hydrocarbyl, 2-hydroxy ethyl, 2-hydroxy propyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is a straight $C_{11-15}$ alkyl or alkenyl chain such as coconut alkyl or mixtures thereof, and Z is derived from a reducing sugar such as glucose, fructose, maltose, lactose, in a reductive amination reaction.

When included in such laundry detergent compositions, the nonionic surfactant systems of the present invention act to improve the greasy/oily stain removal properties of such laundry detergent compositions across a broad range of laundry conditions.

Highly preferred anionic surfactants include alkyl alkoxylated sulfate surfactants hereof are water soluble salts or acids of the formula RO(A)$_m$SO3M wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted ammonium cation. Alkyl ethoxylated sulfates as well as alkyl propoxylated sulfates are contemplated herein. Specific examples of substituted ammonium cations include methyl-, dimethyl, trimethyl-ammonium cations and quaternary ammonium cations such as tetramethyl-ammonium and dimethyl piperdinium cations and those derived from alkylamines such as ethylamine, diethylamine, triethylamine, mixtures thereof, and the like. Exemplary surfactants are $C_{12}$–$C_{18}$ alkyl polyethoxylate (1.0) sulfate ($C_{12}$–$C_{18}$E(1.0)M), $C_{12}$–$C_{18}$ alkyl polyethoxylate (2.25) sulfate ($C_{12}$–$C_{18}$E(2.25)M), $C_{12}$–$C_{18}$ alkyl polyethoxylate (3.0) sulfate ($C_{12}$–$C_{10}$E(3.0)M), and $C_{12}$–$C_{18}$ alkyl polyethoxylate (4.0) sulfate ($C_{12}$–$C_{18}$E(4.0)M), wherein M is conveniently selected from sodium and potassium.

Suitable anionic surfactants to be used are alkyl ester sulfonate surfactants including linear esters of $C_8$–$C_{20}$ carboxylic acids (i.e., fatty acids) which are sulfonated with gaseous $SO_3$ according to "The Journal of the American Oil Chemists Society", 52 (1975), pp. 323–329. Suitable starting materials would include natural fatty substances as derived from tallow, palm oil, etc.

The preferred alkyl ester sulfonate surfactant, especially for laundry applications, comprise alkyl ester sulfonate surfactants of the structural formula:

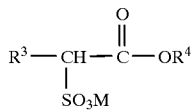

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethanolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other suitable anionic surfactants include the alkyl sulfate surfactants hereof are water soluble salts or acids of the formula ROSO$_3$M wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of $C_{12}$–$C_{16}$ are preferred for lower wash temperatures (e.g. below about 50° C.) and $C_{16-18}$ alkyl chains are preferred for higher wash temperatures (e.g. above about 50° C.).

Other anionic surfactants useful for detersive purposes can also be included in the laundry detergent compositions of the present invention. These can include salts (including, for example, sodium, potassium, ammonium, and substituted ammonium salts such as mono-, di- and triethanolamine salts) of soap, $C_8$–$C_{22}$ primary of secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the formula RO(CH$_2$CH$_2$O)$_k$—CH$_2$COO—M+ wherein R is a $C_8$–$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil.

Further examples are described in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference).

When included therein, the laundry detergent compositions of the present invention typically comprise from about 1% to about 40%, preferably from about 3% to about 20% by weight of such anionic surfactants.

The laundry detergent compositions of the present invention may also contain cationic, ampholytic, zwitterionic, and semi-polar surfactants, as well as the nonionic and/or anionic surfactants other than those already described herein. Preferred cationic surfactant systems include non-ionic and ampholytic surfactants.

Cationic detersive surfactants suitable for use in the laundry detergent compositions of the present invention are those having one long-chain hydrocarbyl group. Examples of such cationic surfactants include the ammonium surfactants such as alkyldimethylammonium halogenides, and those surfactants having the formula:

$$[R^2(OR^3)_y][R^4(OR^3)_y]_2R^5N+X-$$

wherein $R^2$ is an alkyl or alkyl benzyl group having from about 8 to about 18 carbon atoms in the alkyl chain, each $R^3$ is selected from the group consisting of $-CH_2-CH_2-$, $CH_2CH(CH_3)-$, $-CH_2CH(CH_2OH)-$, $-CH_2CH_2CH_2-$, and mixtures thereof; each $R^4$ is selected from the group consisting of $C_1-C_4$ alkyl, $C_1-C_4$ hydroxyalkyl, benzyl ring structures formed by joining the two $R^4$ groups, $-CH_2CHOH-CHOHCOR^6CHOHCH_2OH$ wherein $R^6$ is any hexose or hexose polymer having a molecular weight less than about 1000, and hydrogen when y is not 0; $R^5$ is the same as $R^4$ or is an alkyl chain wherein the total number of carbon atoms of $R^2$ plus $R^5$ is not more than about 18; each y is from 0 to about 10 and the sum of the y values is from 0 to about 15; and X is any compatible anion.

Highly preferred cationic surfactants are the water-soluble quaternary ammonium compounds useful in the present composition having the formula:

$$R_1R_2R_3R_4N^+X^- \quad (i)$$

wherein $R_1$ is $C_8-C_{16}$ alkyl, each of $R_2$, $R_3$ and $R_4$ is independently $C_1-C_4$ alkyl, $C_1-C_4$ hydroxy alkyl, benzyl, and $-(C_2H_{4O})_xH$ where x has a value from 2 to 5, and X is an anion. Not more than one of $R_2$, $R_3$ or $R_4$ should be benzyl.

The preferred alkyl chain length for $R_1$ is $C_{12}-C_{15}$ particularly where the alkyl group is a mixture of chain lengths derived from coconut or palm kernel fat or is derived synthetically by olefin build up or OXO alcohols synthesis.

Preferred groups for $R_2R_3$ and $R_4$ are methyl and hydroxyethyl groups and the anion X may be selected from halide, methosulphate, acetate and phosphate ions.

Examples of suitable quaternary ammonium compounds of formulae (i) for use herein are:
coconut trimethyl ammonium chloride or bromide;
coconut methyl dihydroxyethyl ammonium chloride or bromide;
decyl triethyl ammonium chloride;
decyl dimethyl hydroxyethyl ammonium chloride or bromide;
$C_{12-15}$ dimethyl hydroxyethyl ammonium chloride or bromide;
coconut dimethyl hydroxyethyl ammonium chloride or bromide;
myristyl trimethyl ammonium methyl sulphate;
lauryl dimethyl benzyl ammonium chloride or bromide;
lauryl dimethyl (ethenoxy)$_4$ ammonium chloride or bromide;
choline esters (compounds of formula (i) wherein $R_1$ is

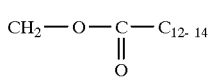

alkyl and $R_2R_3R_4$ are methyl).
di-alkyl imidazolines [compounds of formula (i)].

Other cationic surfactants useful herein are also described in U.S. Pat. No. 4,228,044, Cambre, issued Oct. 14, 1980.

When included therein, the laundry detergent compositions of the present invention typically comprise from 0% to about 25%, preferably from about 3% to about 15% by weight of such cationic surfactants.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. Pat. No. 3,929,678 to Laughlin et al., issued Dec. 30, 1975 at column 19, lines 18–35, for examples of ampholytic surfactants.

When included therein, the laundry detergent compositions of the present invention typically comprise from 0% to about 15%, preferably from about 1% to about 10% by weight of such ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 to Laughlin et al., issued Dec. 30, 1975 at column 19, line 38 through column 22, line 48, for examples of zwitterionic surfactants.

When included therein, the laundry detergent compositions of the present invention typically comprise from 0% to about 15%, preferably from about 1% to about 10% by weight of such zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula

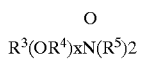

$$R^3(OR^4)xN(R^5)_2$$

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3; and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_1$–$C_{18}$ alkyl dimethyl amine oxides and $C_8$–$C_{12}$ alkoxy ethyl dihydroxy ethyl amine oxides.

When included therein, the laundry detergent compositions of the present invention typically comprise from 0% to about 15%, preferably from about 1% to about 10% by weight of such semi-polar nonionic surfactants.

The present invention further provides laundry detergent compositions comprising at least 1% by weight, preferably from about 3% to about 65%, more preferably from about 10% to about 25% by weight of total surfactants.

OPTIONAL DETERGENT INGREDIENTS

Preferred detergent compositions of the present invention may further comprise an enzyme which provide fabric care benefits. Said enzymes include enzymes selected from cellulases, peroxidases or mixtures thereof.

The cellulases usable in the present invention include both bacterial or fungal cellulase. Preferably, they will have a pH optimum of between 5 and 9.5. Suitable cellulases are disclosed in U.S. Pat. No. 4,435,307, Barbesgoard et al, which discloses fungal cellulase produced from Humicola insolens. Suitable cellulases are also disclosed in GB-A-2.075.028; GB-A-2.095.275 and DE-OS-2.247.832.

Examples of such cellulases are cellulases produced by a strain of Humicola insolens (Humicola grisea var. thermoidea), particularly the Humicola strain DSM 1800.

Other suitable cellulases are cellulases originated from Humicola insolens having a molecular weight of about 50 KDa, an isoelectric point of 5.5 and containing 415 amino acids. Such cellulase are described in Copending European patent application No. 93200811.3, filed Mar. 19, 1993. Especially suitable cellulase are the cellulase having color care benefits. Examples of such cellulases are cellulase described in European patent application No. 91202879.2, filed Nov. 6, 1991 (Novo).

Peroxidase enzymes are used in combination with oxygen sources, e.g. percarbonate, perborate, persulfate, hydrogen peroxide, etc. They are used for "solution bleaching", i.e. to prevent transfer of dyes or pigments removed from substrates during wash operations to other substrates in the wash solution. Peroxidase enzymes are known in the art, and include, for example, horseradish peroxidase, ligninase, and haloperoxidase such as chloro- and bromo-peroxidase. Peroxidase-containing detergent compositions are disclosed, for example, in PCT International Application WO 89/099813 and in European Patent application EP No. 91202882.6, filed on Nov. 6, 1991.

Said cellulases and/or peroxidases are normally incorporated in the detergent composition at levels from 0.0001% to 2% of active enzyme by weight of the detergent composition.

Other preferred enzymes that can be included in the detergent compositions of the present invention include lipases. Suitable lipase enzymes for detergent usage include those produced by microorganisms of the Pseudomonas group, such as *Pseudomonas stutzeri* ATCC 19.154, as disclosed in British Patent 1,372,034. Suitable lipases include those which show a positive immunological cross-reaction with the antibody of the lipase, produced by the microorganism *Pseudomonas fluorescent* IAM 1057. This lipase is available from Amano Pharmaceutical Co. Ltd., Nagoya, Japan, under the trade name Lipase P "Amano," hereinafter referred to as "Amano-P". Especially suitable lipases are lipases such as M1 Lipase® (Gist-Brocades) and Lipolase® (Novo) which have found to be very effective when used in combination with the compositions of the present invention.

The lipases are normally incorporated in the detergent composition at levels from 0.0001% to 2% of active enzyme by weight of the detergent composition.

Other detergent ingredients that can be included are detersive enzymes which can be included in the detergent formulations for a wide variety of purposes. Amylases can be included for removal of carbohydrate-based stains, e.g. Termamyl® (Novo Nordisk)

Other types of enzymes e.g oxidases, reductases, pectinases may also be included. They may be of any suitable origin, such as vegetable, animal, bacterial, fungal and yeast origin.

Said enzymes are normally incorporated in the detergent composition at levels from 0.0001% to 2% of active enzyme by weight of the detergent composition.

Other suitable detergent ingredients that can be added are enzyme oxidation scavengers which are described in Copending European Patent application N 92870018.6 filed on Jan. 31, 1992. Examples of such enzyme oxidation scavengers are ethoxylated tetraethylene polyamines.

Especially preferred detergent ingredients are combinations with technologies which also provide a type of color care benefit. Examples of these technologies are metallo catalysts for color maintenance. Such metallo catalysts are described in copending European Patent Application No. 92870181.2.

Additional optional detergent ingredients that can be included in the detergent compositions of the present invention include bleaching agents. These bleaching agent components can include one or more oxygen bleaching agents and, depending upon the bleaching agent chosen, one or more bleach activators. When present oxygen bleaching compounds will typically be present at levels of from about 1% to about 10%, with a maximum of 1% $AvO_2$ of the detergent composition. Herewith is defined as ubstantial agent composition substantially free of bleach according to the invention. In general, bleaching compounds are optional components in non-liquid formulations, e.g. granular detergents.

The bleaching agent component for use herein can be any of the bleaching agents useful for detergent compositions including oxygen bleaches as well as others known in the art.

The bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. No. 4,483,781, U.S. patent application Ser. No. 740,446, European Patent Application 0,133,354 and U.S. Pat. No. 4,412,934. Highly preferred bleaching agents also include 6-nonylamino-6-oxoperoxycaproic acid as described in U.S. Pat. No. 4,634,551.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

The hydrogen peroxide releasing agents can be used in combination with bleach activators such as tetraacetylethylenediamine (TAED), nonanoyloxybenzenesulfonate (NOBS, described in U.S. Pat. No. 4,412,934), 3,5,-trimethylhexanoloxybenzenesulfonate (ISONOBS, described in EP 120,591) or pentaacetylglucose (PAG), which are perhydrolyzed to form a peracid as the active bleaching species, leading to improved bleaching effect. Also suitable activators are acylated citrate esters such as disclosed in Copending European Patent Application No. 91870207.7.

The hydrogen peroxide may also be present by adding an enzymatic system (i.e. an enzyme and a substrate therefore) which is capable of generating hydrogen peroxide at the beginning or during the washing and/or rinsing process. Such enzymatic systems are disclosed in EP Patent Application 91202655.6 filed Oct. 9, 1991.

Other peroxygen bleaches suitable for the present invention include organic peroxyacids such as percarboxylic acids.

Bleaching agents other than oxygen bleaching agents are also known in the art and can be utilized herein. One type of non-oxygen bleaching agent of particular interest includes photoactivated bleaching agents such as the sulfonated zinc and/or aluminum phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent compositions will contain about 0.025% to about 1.25%, by weight, of sulfonated zinc phthalocyanine.

The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g. SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenlegenschrift 2,446,686, and 2,446,687 and U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2-ethane tetracarboxylates, 1,1,3,3-propane tetracarboxylates and 1,1,2,3-propane tetracarboxylates. Polycarboxylates containing sulfo substituents include the sulfosuccinate derivatives disclosed in British Patent Nos. 1,398,421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis,cis-tetracarboxylates, cyclopentadienide pentacarboxylates, 2,3,4,5-tetrahydro-furan-cis, cis, cis-tetracarboxylates, 2,5-tetrahydro-furan-cis-dicarboxylates, 2,2,5,5-tetrahydrofuran-tetracarboxylates, 1,2,3,4,5,6-hexane -hexacarboxylates and carboxymethyl derivatives of polyhydric alcohols such as sorbitol, mannitol and xylitol. Aromatic poly-carboxylates include mellitic acid, pyromellitic acid and the phthalic acid derivatives disclosed in British Patent No. 1,425,343.

Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

A suitable chelant for inclusion in the detergent compositions in accordance with the invention is ethylenediamine-N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include $Na_2EDDS$ and $Na_4EDDS$. Examples of such preferred magnesium salts of EDDS include MgEDDS and $Mg_2EDDS$. The magnesium salts are the most preferred for inclusion in compositions in accordance with the invention.

Preferred builder systems include a mixture of a water-insoluble aluminosilicate builder such as zeolite A, and a watersoluble carboxylate chelating agent such as citric acid. Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated from each other by not more than two carbon atoms. Polymers of this type are disclosed in GB-A-1,596,756. Examples of such salts are polyacrylates of MW 2000–5000 and their copolymers with maleic anhydride, such copolymers having a molecular weight of from 20,000 to 70,000, especially about 40,000.

Detergency builder salts are normally included in amounts of from 10% to 80% by weight of the composition preferably from 20% to 70% and most usually from 30% to 60% by weight.

Another optional ingredient is a suds suppressor, exemplified by silicones, and silica-silicone mixtures. Silicones can be generally represented by alkylated polysiloxane materials while silica is normally used in finely divided forms exemplified by silica aerogels and xerogels and hydrophobic silicas of various types. These materials can be incorporated as particulates in which the suds suppressor is advantageously releasably incorporated in a water-soluble or water-dispersible, substantially nonsurface-active detergent impermeable carrier. Alternatively the suds suppressor can be dissolved or dispersed in a liquid carrier and applied by spraying on to one or more of the other components.

A preferred silicone suds controlling agent is disclosed in Bartollota et al. U.S. Pat. No. 3,933,672. Other particularly useful suds suppressors are the self-emulsifying silicone suds suppressors, described in German Patent Application DTOS 2 646 126 published Apr. 28, 1977. An example of such a compound is DC-544, commercially available from Dow Corning, which is a siloxane-glycol copolymer. Especially preferred suds controlling agent are the suds suppressor system comprising a mixture of silicone oils and 2-alkyl-alcanols. Suitable 2-alkyl-alkanols are 2-butyl-octanol which are commercially available under the trade name Isofol 12 R. Such suds suppressor system are described in Copending European Patent application N 92870174.7 filed Nov. 10, 1992.

Especially preferred silicone suds controlling agents are described in Copending European Patent application N°92201649.8. Said compositions can comprise a silicone/silica mixture in combination with fumed nonporous silica such as Aerosil®.

The suds suppressors described above are normally employed at levels of from 0.001% to 2% by weight of the composition, preferably from 0.01% to 1% by weight.

Other components used in detergent compositions may be employed, such as soil-suspending, agents soil-release agents, optical brighteners, abrasives, bactericides, tarnish inhibitors, coloring agents, and/or encapsulated or non-encapsulated perfumes.

Especially suitable encapsulating materials are water soluble capsules which consist of a matrix of polysaccharide and polyhydroxy compounds such as described in GB 1,464,616.

Other suitable water soluble encapsulating materials comprise dextrins derived from ungelatinized starch acid-esters of substituted dicarboxylic acids such as described in U.S. Pat. No. 3,455,838. These acid-ester dextrins are, preferably, prepared from such starches as waxy maize, waxy sorghum, sago, tapioca and potato. Suitable examples of said encapsulating materials include N-Lok manufactured by National Starch. The N-Lok encapsulating material consists of a modified maize starch and glucose. The starch is modified by adding monofunctional substituted groups such as octenyl succinic acid anhydride.

Other suitable detergent ingredients that can be added to the compositions of the present invention include fabric softening clays such as described in European Patent application No. 522 206.

Antiredeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydrideacrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably from 0.75% to 8%, most preferably from 1% to 6% by weight of the composition.

Preferred optical brighteners are anionic in character, examples of which are disodium 4,4'-bis-(2-diethanolamino-4-anilino -s-triazin-6-ylamino)stilbene-2:2'disulphonate, disodium 4, -4'-bis-(2-morpholino-4-anilino-s-triazin-6-ylaminostilbene-2:2'-disulphonate, disodium 4,4'-bis(2,4-dianilino-s-triazin-6-ylamino)stilbene-2:2'-disulphonate, monosodium 4',4"-bis-(2,4-dianilino-s-triazin-6-ylamino) stilbene-2-sulphonate, disodium 4,4'-bis(2-anilino-4-(N-methyl-N-2-hydroxyethylamino)-s-triazin-6ylamino) stilbene-2,2'-disulphonate, disodium 4,4'-bis-(4-phenyl-2,1, 3-triazol-2-yl)-stilbene-2,2' disulphonate, disodium 4,4'bis (2-anilino-4-(1-methyl-2-hydroxyethylamino)s-triazin-6-ylamino)stilbene-2,2'disulphonate and sodium 2(stilbyl-4"-(naphtho-1',2':4,5)-1,2,3 -triazole-2"-sulphonate.

Other useful polymeric materials are the polyethylene glycols, particularly those of molecular weight 1000–10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in the commonly assigned U.S. Pat. Nos. 4116885 and 4711730 and European Published Patent Application No. 0 272 033. A particular preferred polymer in accordance with EP-A-0 272 033 has the formula $(CH_3(PEG)_{43})_{0.75}(POH)_{0.25}[T-PO]_{2.8}(T-PEG)_{0.4}]T(PO-H)_{0.25}((PEG)_{43}CH_3)_{0.75}$ where PEG is —$(OC_2H_4)O$—, PO is $(OC_3H_6O)$ and T is 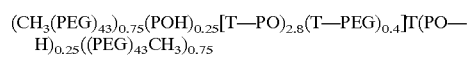

Also very useful are modified polyesters as random copolymers of dimethyl terephthalate, dimethyl sulfoisophthalate, ethylene glycol and 1-2 propane diol, the end groups consisting primarily of sulphobenzoate and secondarily of mono esters of ethylene glycol and/or propanediol. The target is to obtain a polymer capped at both end by sulphobenzoate groups, "primarily", in the present context most of said copolymers herein will be end-capped by sulphobenzoate groups. However, some copolymers will be less than fully capped, and therefore their end groups may consist of monoester of ethylene glycol and/or propane 1-2 diol, thereof consist "secondarily" of such species.

The selected polyesters herein contain about 46% by weight of dimethyl terephthalic acid, about 16% by weight of propane −1.2 diol, about 10% by weight ethylene glycol about 13% by weight of dimethyl sulfobenzoic acid and about 15% by weight of sulfoisophthalic acid, and have a molecular weight of about 3.000. The polyesters and their method of preparation are described in detail in EPA 311 342.

The present invention also relates to a process for inhibiting dye transfer from one fabric to another of solubilized and suspended dyes encountered during fabric laundering operations involving colored fabrics.

The process comprises contacting fabrics with a laundering solution as hereinbefore described.

The process of the invention is conveniently carried out in the course of the washing process. The washing process is preferably carried out at 5° C. to 95° C., especially between 10° C. and 60° C., but the polymers are effective at up to 95° C. and higher temperatures. The pH of the treatment solution is preferably from 7 to 11, especially from 7.5 to 10.5.

The process and compositions of the invention can also be used as detergent additive products. Such additive products are intended to supplement or boost the performance of conventional detergent compositions.

The detergent compositions according to the present invention include compositions which are to be used for cleaning substrates, such as fabrics, fibers, hard surfaces, skin etc., for example hard surface cleaning compositions (with or without abrasives), laundry detergent compositions, automatic and non automatic dishwashing compositions.

The following examples are meant to exemplify compositions of the present invention, but are not necessarily meant to limit or otherwise define the scope of the invention, said scope being determined according to claims which follow.

EXAMPLE I

WOOL DAMAGE
(Launderometer experiments/40° C./Benetton fabric: 78% wool/ 22% Angorra)

|  |  | pH 10.5 |
| --- | --- | --- |
| DETERGENT COMPOSITION* A and B |  | 0 |
| NO PROTEASE |  |  |
| WITH PARENT ENZYME(1) | 1X$^{(2)}$ | 5 |
| WITH VARIANTS |  |  |
| • V104Y | 1X | 4.5 |
| • N76D | 1X | 4 |
|  | ½X | 3.5 |
| • N76D/V104I | ½X | 3 |
| • N76D/N123S | ½X | 4 |
| • N76D/V104I/N123S | ½X | 2 |
| • N76D/S103A/V104I/N123S | ½X | 2 |
| • K27R/V104Y/N123S/T274A | 1X | 1.5 |
|  | ½X | 0.5 |

RANKING
0 = no damage
1 = hardly detectable damage
2 = slight damage
3 = clearly strong damage
4 = high damage
5 = destruction
(*)Detergent compositions A and B given in Example II;
(1)amino acid sequence as given in Figure 1;
$^{(2)}$1X = 16 mg active enzyme protein/100 g detergent composition;

The above result clearly shows that currently commercial available alkaline proteases have a severe damaging effect on the proteinaceous fabrics like wool and/or silk. With the above mentioned mutations the specific activity of high alkaline proteases for such fabrics (leading to damage) shows an increased compatibility for said fabrics. Net results are:

1) excellent cleaning and stain removal;

2) good fabric compatibility.

EXAMPLE II

DETERGENT COMPOSITIONS
Granular fabric cleaning compositions

|  | EXAMPLE No. | |
| --- | --- | --- |
| COMPONENTS | A | B |
| Linear alkyl benzene sulphonate | 11.4 | 10.70 |
| Tallow alkyl sulphate | 1.80 | 2.40 |
| $C_{14-15}$ alkyl sulphate | 3.00 | 3.10 |
| $C_{14-15}$ alcohol 7 times ethoxylated | 4.00 | 4.00 |
| Tallow alcohol 11 times ethoxylated | 1.80 | 1.80 |
| Dispersant | 0.07 | 0.1 |
| Silicone fluid | 0.80 | 0.80 |
| Trisodium citrate | 14.00 | 15.00 |
| Citric acid | 3.00 | 2.50 |
| Zeolite | 32.50 | 32.10 |
| Maleic acid acrylic acid copolymer | 5.00 | 5.00 |
| Diethylene triamine penta methylene phosphonic acid | 1.00 | 0.20 |
| Protease (active protein) | 0.02 | 0.01 |
| Lipase (Lipolase 100T) | 0.36 | 0.40 |
| Amylase (Termamyl 60T) | 0.30 | 0.30 |
| Sodium silicate | 2.00 | 2.50 |
| Sodium sulphate | 3.50 | 5.20 |
| Polyvinyl pyrrolidone | 0.30 | 0.50 |
| Perborate tetrahydrate | — | 1 |
| Phenol sulphonate | — | 0.2 |
| Peroxidase | — | 0.1 |
| Minors | Up to 100 | Up to 100 |

Liquid fabric cleaning compositions

|  | EXAMPLE NO. | |
| --- | --- | --- |
| COMPONENT | A | B |
| $C_{12-14}$ alkenyl succinic acid | 3.0 | 8.0 |
| Citric acid monohydrate | 10.0 | 15.0 |
| Sodium $C_{12-15}$ alkyl sulphate | 8.0 | 8.0 |
| Sodium sulfate of $C_{12-15}$ alcohol 2 times ethoxylated | — | 3.0 |
| $C_{12-15}$ alcohol 7 times ethoxylated | — | 8.0 |
| $C_{12-15}$ alcohol 5 times ethoxylated | 8.0 | — |
| Diethylene triamine penta (methylene phosphonic acid) | 0.2 | — |
| Oleic acid | 1.8 | — |
| Ethanol | 4.0 | 4.0 |
| Propanediol | 2.0 | 2.0 |
| Protease (active protein) | 0.02 | 0.02 |
| Polyvinyl pyrrolidone | 1.0 | 2.0 |
| Suds suppressor | 0.15 | 0.15 |
| NaOH | up to pH 7.5 | |
| Waters and minors | up to 100 parts | |

What is claimed is:

1. A wool and fabric cleaning composition substantially free of bleach and comprising:
   (a) a polymeric dye transfer inhibiting agents;
   (b) a mutant of a high alkaline protease having at least 70% homology with the amino acid sequence according to FIG. 1 differing by at least one mutation in each of the regions 96–110 and 123–135;
   (c) from about 3% to about 15%, by weight, cationic surfactant;
   (d) from about 1% to about 40%, by weight, anionic surfactant; and
   (e) a nonionic surfactant which is at least one ethoxylated alcohol.

2. A wool and fabric cleaning composition according to claim 1 wherein the protease has at least one additional mutation.

3. A wool and fabric cleaning composition according to claim 2 wherein the at least one additional mutation is at a position selected from the group consisting of 27, 76, 99, 101, 103, 222, 274 and mixtures thereof.

4. A wool and fabric cleaning composition according to claim 3 wherein the at least one additional mutation is selected from the group consisting of K27R, S99D, S101R, S103A, M222S, M222A, M222C, T274A and mixtures thereof.

5. A wool and fabric cleaning composition according to claim 1 wherein the polymeric dye transfer agent is selected from the group consisting of polyamine N-oxide polymers, copolymers of N-vinylpyrrolidone and N-vinylimidazole, polyvinylpyrrolidones, polyvinyloxazolidones, polyvinylimidazoles and mixtures thereof.

6. A wool and fabric cleaning composition according to claim 1 further comprising an enzyme selected from the group consisting of cellulases, peroxidases and mixtures thereof.

7. A wool and fabric cleaning composition according to claim 1, comprising from about 3% to about 20%, by weight, anionic surfactant.

8. A wool and fabric cleaning composition according to claim 7, wherein the density of the composition measured at 20° C. is from 600 to 900 g/liter and the composition comprises no more than 5%, by weight, filler salt.

9. A wool and fabric cleaning composition according to claim 1, wherein the cationic surfactant is selected from the group consisting of:
   (a) alkyldimethylammonium halogenides;
   (b) water-soluble quaternary ammonium compounds; and
   (c) mixtures thereof.

10. A wool and fabric cleaning composition according to claim 7, further comprising a surfactant selected from the group consisting of:
    (a) ampholytic surfactants at a level of from 1% to 10%, by weight of the composition;
    (b) zwitterionic surfactants at a level of from 1% to 10%, by weight of the composition; and
    (c) mixtures thereof.

11. A detergent composition substantially free of bleach and comprising:
    (a) a polymeric dye transfer inhibiting agent;
    (b) a mutant of a high alkaline protease which comprises mutations N76D, V104I or V104I, and N123S;
    (c) softening clay;
    (d) anionic brightener; and
    (e) a nonionic surfactant which is at least one ethoxylated alcohol.

12. A detergent composition according to claim 11, further comprising from about 1% to about 40%, by weight, anionic surfactant, from about 3% to about 15%, by weight, cationic surfactant and no more than 5%, by weight, filler salt; and wherein the density of the composition measured at 20° C. is from 600 to 900 g/liter.

13. A detergent composition according to claim 12, further comprising from 0.25% to 2.5%, by weight, polyethylene glycol having a molecular weight of from 2000 to 8000 and from 0.001% to 2%, by weight, of a suds suppressor comprising silicone oil and 2-alkyl-alcanol.

14. A detergent composition according to claim 11, further comprising a chelant selected from the group consisting of magnesium salts of ethylenediamine-N,N'-disuccinic acid.

15. A method of reducing damage to wool and silk fabrics during washing, comprising the step of washing the fabric with a wool and fabric cleaning composition of claim 1.

16. A method according to claim 15, wherein the wool and fabric cleaning composition further comprises softening clay and anionic brightener.

17. A method according to claim 15, wherein the wool and fabric cleaning composition further comprises from 0.001% to 2%, by weight, of a suds suppressor comprising silicone oil and 2-alkyl-alcanol.

* * * * *

UNITED STATES PATENT AND TRADEMARK OFFICE
CERTIFICATE OF CORRECTION

PATENT NO. : 5,922,082
DATED : July 13, 1999
INVENTOR(S) : Andre Cesar Baeck et al.

It is certified that error appears in the above-identified patent and that said Letters Patent is hereby corrected as shown below:

Column 23, claim 1, component (b) should read -- a mutant of a high alkaline protease which comprises mutations N76D, V104I or V104Y, and N123S; --.

Column 23, claim 3 should read -- A wool and fabric cleaning composition according to claim 2 wherein the at least one additional mutation is at a position selected from the group consisting of 27, 99, 101, 103, 222, 274 and mixtures thereof. --.

Signed and Sealed this

Sixteenth Day of May, 2000

Attest:

Q. TODD DICKINSON

Attesting Officer

Director of Patents and Trademarks